United States Patent [19]
Mahe et al.

[11] Patent Number: 5,885,766
[45] Date of Patent: Mar. 23, 1999

[54] METHOD OF SCREENING OF SUBSTANCES FOR THEIR EFFECT ON THE EXPRESSION OF MEDIATORS OF INFLAMMATION IN A HAIR FOLLICLE

[75] Inventors: Yann Mahe, Morsang sur Orge; Nelly Billoni, Paris; Jean-François Michelet, Creteil, all of France

[73] Assignee: Société L'Oréal S.A., Paris, France

[21] Appl. No.: 927,538

[22] PCT Filed: Sep. 26, 1995

[86] PCT No.: PCT/JP95/01940

§ 371 Date: Jun. 6, 1996

§ 102(e) Date: Jun. 6, 1996

[87] PCT Pub. No.: WO96/11421

PCT Pub. Date: Apr. 18, 1996

Related U.S. Application Data

[63] Continuation of Ser. No. 603,122, Feb. 20, 1996, abandoned.

[30] Foreign Application Priority Data

Feb. 17, 1995 [FR] France .................................. 95 01880

[51] Int. Cl.$^6$ .............................. A01N 1/02; C12Q 1/02; C12N 5/00
[52] U.S. Cl. ................................ 435/1.1; 435/29; 435/375
[58] Field of Search .............................. 435/1.1, 29, 375; 424/70.1

[56] References Cited

U.S. PATENT DOCUMENTS 5,229,271  7/1993  Philpott .................................... 435/29
5,279,969  1/1994  Lavrer et al. ............................. 436/63
5,712,169  1/1998  Bernard et al. ......................... 436/503

FOREIGN PATENT DOCUMENTS 0434319  6/1991  European Pat. Off. .

OTHER PUBLICATIONS

Brannan PG et al., J. Lipid Res. 16: 7–11 (1975).
Hoffmann R et al., J. Invest. Dermatology 103(4): 530–33 (1994).
Arase S et al., J. Dermatol. Sci 2(5):353–360 (1991).
FASEB Journal, vol. 6, No. 3, 1992 Washington, D.C., pp. 911–913, J.J. Jimenez et al, Interleukin 1 protects hair follicles . . . , p. 911, col. 1, lines 1–9, p. 912, col. 1, lines 13–28.

*Primary Examiner*—Sandra E. Saucier
*Attorney, Agent, or Firm*—Burns, Doane, Swecker & Mathis, L.L.P.

[57] ABSTRACT

An assay for determining whether a first substance is potentially suitable for use as an active agent in hair treating compositions is provided. This assay involves contacting a first substance having putative activity as an active agent for treating hair with plucked hair follicle contained in a culture medium and assaying for a second substance which is correlated to the potential efficacy of the first substance. This assay is particularly suitable for use in evaluating the potential efficacy of hair growth promoters, hair growth retardants, agents that affect hair color, agents that affect hair survival and agents that affect inflammation. This assay is especially suited for evaluating putative efficacy of agents for treatment and/or prevention of the inflammatory stages of alopecia. In particular, the compound to be quantitatively determined is a mediator of inflammation.

28 Claims, No Drawings

METHOD OF SCREENING OF SUBSTANCES FOR THEIR EFFECT ON THE EXPRESSION OF MEDIATORS OF INFLAMMATION IN A HAIR FOLLICLE

This application is a continuation of application Ser. No. 08/603,122, filed Feb. 20, 1996 now abandonded.

The subject of the invention is a process for testing a substance, the said substance possibly being active in the hair field.

Hair field is understood to mean everything which can relate to the hair of an individual. Thus, "substance which is possibly active in the hair field", or simply "substance" subsequently in the text, is understood to mean any molecule or collection of molecules exhibiting a potential activity in the hair field and in particular any molecule or collection of molecules potentially having an activity on the colouring, the survival, the slowing down or halting of the growth, the loss or alternatively the intensified growth of hair follicles. The substance to be tested can be used according to the process of the invention either in its molecular form or in the form of a composition containing the molecule to be tested.

To date, the prior art mentions two main methods for testing for a substance which is possibly active in the hair field. The first consists in carrying out tests on volunteers and observing more or less rapidly the effects of the tested substance. It is obvious that this method has many disadvantages, including in particular that of being applied to human beings, which obviously limits, for ethical reasons, the field of application of the method. Thus, the number and the quality of the substances tested is limited. Moreover, these tests are generally cumbersome to carry out and extend over lengthy time periods. The results of the test are then in the majority of cases observations of phenotypic modifications of the hair follicle.

The second method known in the prior art is that described in Patent EP 434,319. This method consists in carrying out the tests according to a process which involves four stages, including in particular a stage of isolation of a viable hair follicle which has retained an intact bulb. To do this, it proves necessary to carry out a microdissection of the hair follicle, from a sample withdrawn from a subject. The latter in any case retains a mark of this operation. This limits the supply of hair follicles and the implementation of the test method is cumbersome and lengthy.

After much work, the Applicant Company has been able to show that it is possible to use, in the hair field, at least one plucked hair follicle for testing a substance which is possibly active in the hair field.

The subject of the invention is therefore a process for testing a substance which is possibly active in the hair field, characterized in that at least one hair follicle which has been plucked from a subject is incubated in a suitable culture medium for a sufficient time, in that this plucked hair follicle is brought into contact with a substance which is possibly active in the hair field, in that a label of the activity of the said tested substance is quantitatively determined and in that the results of the quantitative determination are evaluated with respect to a control.

The hair follicle used in the process according to the invention was isolated by plucking. The plucking consists of a sudden separation of the hair follicle and of the dermis, generally carried out by a more or less strong pull exerted on the hair shaft of the follicle.

The plucked hair follicle can be intact, that is to say contain all the parts recognized by the person skilled in the art as constituting it (see, in this respect, "Science des traitements capillaires" [Science of Hair Treatments], Charles Zviak, published by Masson, 1987). Mention will be made, for example, and nonlimitingly, among these parts, of the dermal papillae, the hair bulb, the epithelial sheaths and the sebaceous gland. However, of course, the invention is not limited to the intact plucked hair follicle and also relates to any plucked hair follicle which, after isolation, would have retained only a portion of its constituent parts.

Plucking in order to isolate the hair follicle is a particularly advantageous procedure since it has the advantages of being noninvasive and therefore nontraumatizing for the subject and of being simple and fast to carry out.

An additional advantage lies in the fact that plucking can be carried out by the subject himself and anywhere, which places no additional constraint on the subject.

After isolation, the hair follicle is incubated in a suitable culture medium possibly containing the substance to be tested. It is clearly understood that the substance to be tested can be added to the incubation medium at any time, that is to say before or after bringing plucked hairs into contact with the said incubation medium. This medium, which is a nutrient medium, is at least composed of the components necessary for keeping the hair follicle alive.

Of course, it can contain any other necessary component, for example necessary for the growth of the hair follicle as for example insulin, glutamine or hydrocortisone.

Mention may be made, by way of example, as culture medium well known to the person skilled in the art, of Dulbecco's modified medium MEM, Williams' medium E, F12 medium, HAM medium or alternatively RPMI 1640, sold by the company Gibco-BRL, Biomed, Boehringer or alternatively Sigma.

The incubation time is generally conditioned by the time necessary for the hair follicle to respond to the substance which is possibly active in the hair field with which it is brought into contact, that is to say the time necessary in order to see the appearance of a modification in the level of expression of the label of the activity of the tested substance which is being quantitatively determined.

This incubation time can range from a few seconds to a number of days. By way of indication, the incubation time is generally between 5 seconds and 96 hours and preferably between 12 and 24 hours.

Label of the activity of the tested substance which is possibly active in the hair field is understood to mean, according to the invention, any component, the presence, the absence, the modification in the expression or the modification in the distribution of which can be measured in response to bringing the plucked hair follicle into contact with the said substance to be tested. Mention may be made, as an example of a label, and without limitation, of protein, DNA, RNA, organelle, ion, metal, amino acid, lipid and liposoluble compound.

The activity of the substance to be tested is thus represented by the variation in the label of the activity of the tested substance which will have been chosen to be quantitatively determined. Variation is understood to mean any modification in the amount, concentration or distribution of the label which is quantitatively determined.

To do this, the process according to the invention comprises a stage of quantitative determination of the label of the activity of the tested substance.

After incubation, this quantitative determination can be carried out directly on the culture medium for the components excreted by the cell or in the hair follicle for the non-excreted components.

Thus, and more particularly in the case where the component which is being searched for is not excreted, it is possible to envisage an additional stage before quantitative determination, during which the hair follicle is ground, in order to make the label of the activity of the tested substance to be quantitatively determined more accessible.

Very clearly, whatever the embodiment of the process according to the invention, any quantitative determination method known by the person skilled in the art can be used.

It is possible, by way of example and without limitation, to mention the methods of quantitative determination of proteins or of nucleic acids by colorimetry, by electrophoresis, by reverse transcriptase and amplification by the chain polymerization technique, mass spectography, chromatography (in the gas phase or on a plate), immunological methods, or alternatively optical or electron microscopy for measuring the amount of an organelle.

The result of the quantitative determination, which represents the variation in the label of the activity of the tested substance which has been chosen to be quantitatively determined, cannot in itself be directly made use of. It only becomes advantageous in so far as it is compared with the result of the same quantitative determination carried out under the same conditions but without bringing the plucked hair follicle into contact with the substance to be tested. Thus it is that the process according to the invention includes a stage during which an evaluation is carried out of the results of the quantitative determination with respect to a control.

The person skilled in the art easily determines, out of habit, the nature of the control necessary in the implementation of the process.

An advantage of the invention is that it provides, in the hair field, a simultaneously simple, fast and effective method for testing a substance which is possibly active which does not involve invasive stages.

In the hair field, the substances which are possibly active which it is desired to test generally correspond to a modification in the state of the head of hair of the subject and preferentially the present or future state of this head of hair.

Generally, the substances to be tested possibly have an effect either on the colour of the hair follicles or on the density, on the amount or on the quality of the latter. These are substances which possibly have an effect, for example, on the slowing down or halting of the growth, the loss or alternatively the intensified growth of the hair follicles.

Thus, the present invention makes it possible to test substances which are possibly active in the hair field which have an effect on the slowing down or halting of the growth, the loss, the colouring or alternatively the intensified growth of the hair follicles.

The process according to the invention preferentially makes it possible to test substances possibly having an effect on the slowing down or halting of the growth, the loss or the colouring of the hair follicles.

As regards only the slowing down or halting of the growth or the loss of the hair follicles, the eventual consequence for the subject is a more or less pronounced alopecia, which it is known can have aesthetic, psychological and social consequences for the affected subject.

More particularly, the process according to the invention makes it possible to test substances possibly having an effect on the slowing down or halting of the growth or the loss of the hair follicles.

The process according to the invention therefore makes it possible to test substances which are possibly active in the hair field in the treatment of an alopecia.

The term alopecia covers a whole family of attacks on the hair follicle having the consequence, whatever the reason, of the partial or general definitive loss of hair. Mention may be made, for example, of androgenic alopecia, alopecia areata (pelade) or alopecia totalis, or alternatively alopecia universalis.

Without wishing to be bound by any one theory of the invention, it seems that some alopecias pass through at least one inflammatory stage.

An inflammatory stage of alopecia is characterized, inter alia, by a modification in the level of expression of mediators of inflammation.

Thus, the activity of a substance which is possibly active against at least one inflammatory stage of an alopecia can thus be evaluated by the process according to the invention by quantitatively determining, in a hair follicle, at least one of the known mediators of inflammation, after incubation of the hair follicle with the said substance to be tested.

Consequently, after incubation of the hair follicle with the substance to be tested, the label of the activity of the said substance is, in the process according to the invention, advantageously one of the mediators of inflammation.

Mention may be made, among these mediators, of cytokines, including in particular interleukin-1α, interleukin-1β, interleukin-6 or tumour necrosis factors α and β (TNF-α and -β), chemokines, such as interleukin-8 or monocyte chemotactic and activating factor (MCAF), or alternatively other chemotactic factors responsible for the recruitment of lymphocyte, monocyte, Langerhans or basophil cells at the inflammatory site, such as leukotrienes $B_4$, or alternatively other factors involved in the inflammatory cascade, such as arachidonic acid or prostaglandins, including in particular prostaglandins $E_2$.

The Applicant Company has indeed found that, in certain subjects, and in particular in those exhibiting a beginning of alopecia, the level of the interleukins is modified. The level of interleukin-1α and of interleukin-8, and more particularly the level of interleukin-1α, is increased in the majority of subjects showing a beginning of alopecia.

The mediator of inflammation to be quantitatively determined in the process according to the invention is preferentially interleukin-1α and interleukin-8 and more particularly the level of interleukin-1α.

The Applicant Company has also found that, in some subjects exhibiting an advanced alopecia, the level of prostaglandins $E_2$ is higher than in others, suggesting an involvement of this mediator in the progression of this disorder. Thus, an early quantitative determination of any variation in the level of prostaglandins $E_2$ makes it possible to prognosticate a worsening of the alopecia. It is then possible to suggest an appropriate treatment.

Thus, prostaglandins $E_2$ are another mediator of inflammation related to a hair disorder which the process according to the invention can quantitatively determine.

One of the advantages of the invention is thus to provide a simple process for evaluating the activity of a substance which is possibly active against at least one inflammatory stage of an alopecia, which substance could subsequently be used in the preparation of a cosmetic composition or of a medicament for the purpose of treating at least one inflammatory stage of the alopecia.

Another advantage of the invention is to provide a simple means for evaluating the effectiveness of a treatment applied to a subject, by repetitively and regularly making use of the process according to the invention, from a hair follicle plucked from the said subject.

Moreover, the process according to the invention can make it possible to avoid a restrictive, cumbersome and expensive treatment of a specific subject (for example, for whom the alopecia is not or is no longer in the inflammatory stage) or when the test shows a response to this active ingredient in the form of a hyperproduction of inflammatory mediators (phenomena of allergy and/or of irritation).

Moreover, the process according to the invention makes it possible to evaluate the activity of a substance which can be used in the preparation of a cosmetic composition or of a medicament for the purpose of treating at least one inflammatory stage of alopecia.

The Applicant Company has therefore shown, as will be seen in the examples hereinbelow, that vitamin D and its derivatives, and more particularly 1,25-dihydroxyvitamin $D_3$, has an activity against at least one of the mediators of inflammation related to alopecia.

A further subject of the invention is the use of the process according to the invention for evaluating the effectiveness of a treatment applied to a subject.

Examples will now be given by way of illustration which should in no way limit the scope of the invention.

EXAMPLE 1

Inhibiting effect of vitamin $D_3$ on the production of interleukin-1α, induced by interleukin-1β, in a plucked hair follicle.

In order to trigger a process mimicking an inflammatory stage in the plucked hair follicle, which represents the state of the follicle in a subject in the inflammatory stage of alopecia, at least one plucked follicle is incubated in the presence of interleukin-1β.

Ten plucked hairs are withdrawn from the region of the vertex of a volunteer. Five of these hairs are immediately incubated in Williams' medium E (sold by the company Gibco BRL), to which medium are added antibiotics (penicillin G, 100 units/ml; streptomycin S, 100 μg/ml; amphotericin, 250 mg/ml) and interleukin-1β (recombinant marketed by Saxon Biochemicals GmbH) in the proportion of 100 ng/ml. The five other hairs are incubated in the same medium (to which are added antibiotic and interleukin-1β) in the presence of 1,25-dihydroxyvitamin $D_3$ (France Biochem) at the concentration of 0.1 nM.

After incubating for 20 hours, the culture supernatants are collected in a tube and then centrifuged for 5 minutes at 14000 revolutions/minute (Eppendorff centrifuge, model 5415C). The supernatants are then collected in a clean tube and placed at 4° C. The concentration of interleukin-1α is then evaluated for 100 μl of supernatant using an ELISA Biotrak kit marketed by the company Amersham, the recommendations of the supplier being followed.

| | Concentration of IL-1α (in pg/ml) | | |
|---|---|---|---|
| | Control | Control + Vit. $D_3$ | % Inhibition |
| Subject No. 1 | 3.8 | 2.1 | 44 |
| Subject No. 2 | 80.7 | 40.5 | 50 |
| Subject No. 3 | 13.8 | 8.8 | 36 |
| Subject No. 4 | 34.7 | 28.9 | 17 |
| Subject No. 5 | 18 | 12 | 33 |

Statistical analyses were carried out by comparisons of the medians by calculation of the Student's t (D. Schwartz: Méthodes statistiques à l'usage des médecins et des biologistes [Statistical methods for the use of doctors and biologistes]. Flammarion médecine et sciences, 1989).

The null hypothesis ($H_0$) is formulated as being: Control+ Vit. $D_3 \geq$ Control, in the context of a one-sided test, taking into account the fact that it concerns paired values.

According to Student, for the calculated t, there is rejection of $H_0$ at the p=5% threshold. In this case, p=0.001.

Conclusion: Since $H_0$ is rejected, it may be concluded, at the 5% threshold, that the two populations (1: Control and 2: Control+Vit. $D_3$) differ significantly; the results obtained for the population 1 are significantly greater than those obtained with population 2.

The experiment shows that vitamin $D_3$ is a good inhibitor of the production of interleukin-1α, in a system reproducing the inflammatory conditions of a hair follicle.

Consequently, this test can be used to evaluate the anti-inflammatory abilities of other analogues of vitamin $D_3$, by evaluation of their ability to inhibit the production of interleukin-1α.

EXAMPLE 2

Inhibiting effect of vitamin $D_3$ on the production of interleukin-8, induced by interleukin-1α, in a plucked hair follicle.

Fifteen hairs originating from volunteers are withdrawn from the region of the nape of the neck. They are immediately incubated in Williams' medium E, marketed by the company Gibco BRL, to which are added glutamine (2 mM) and antibiotics (penicillin G, 100 units/ml; streptomycin S, 100 μg/ml; amphotericin, 250 ng/ml), in the proportion of 200 μl of medium per plucked hair.

They are then divided into three batches: Batch No. 1: Hairs incubated in the Williams' medium E mentioned above.

Batch No. 2: Hairs incubated in the Williams' medium E mentioned above, to which is added interleukin-1α (Biosource International) to a final concentration of 25 or 100 ng/ml (25 ng/ml for Subject No. 1 or 100 ng/ml for Subjects No. 2 and 3).

Batch No. 3: Hairs incubated in the same medium as Batch No. 2, to which is added 1,25-dihydroxyvitamin $D_3$ to 0.1 nM.

After 20 hours, the culture supernatants are collected in a tube and then centrifuged for 5 minutes at 14000 revolutions/minute (Eppendorff centrifuge, model 5415C). The supernatants are then collected in a clean tube and placed at 40° C.

The concentration of interleukin-8 is then evaluated for 100 μl of supernatant using an ELISA Biotrak kit marketed by the company Amersham, the instructions of the manufacturer being followed.

| | Batch No. 1 | Batch No. 2 | Batch No. 3 | |
|---|---|---|---|---|
| | | IL-8 (in pg/ml) | | % Inhibition |
| Subject No. 1 | 170 | 622 | 251 | 82 |
| Subject No. 2 | 300 | 863 | 353 | 91 |
| Subject No. 3 | 266 | 657 | 496 | 41 |
| Subject No. 4 | 226 | 477 | 356 | 48 |

Statistical analyses were carried out by comparisons of the means or of the medians by application of the Student's t test (D. Schwartz/Méthodes statistiques à l'usage des médecins et des biologistes [Statistical methods for the use of doctors and biologists]. Flammarion médecine et sciences, 1989). The null hypothesis ($H_0$) is formulated as being: Batch No. $3 \geq$ Batch No. 2, in the context of a one-sided test, taking into account the fact that it concerns paired values.

According to Student, for the calculated t, there is rejection of $H_0$ at the p=5% threshold. In this case, p=0.025.

Conclusion: Since $H_0$ is rejected, it may be concluded, at the 5% threshold, that the two batches differ significantly; the results obtained for Batch 2 are significantly greater than those obtained with Batch 3.

In these four cases, an inhibition of the production of interleukin-8 by 1,25-dihydroxyvitamin $D_3$ is observed.

As IL-8 is an inflammatory chemokine induced by interleukin-1α, the test shows that 1,25-dihydroxyvitamin $D_3$, at 0.1 nM, has an antiinflammatory effect on the plucked follicle incubated in the presence of interleukin-1α. Consequently, this test can be used to evaluate the antiinflammatory abilities of other analogues of vitamin $D_3$, by evaluation of their ability to inhibit the production of interleukin-8.

EXAMPLE 3

Inhibiting effect of minoxidil on the production of prostaglandins $E_2$ ($PGE_2$) in a hair follicle isolated by plucking.

10 hairs originating from three alopecic donors and from two non-alopecic donors are withdrawn by plucking, from the region of the vertex. They are immediately divided into two batches: Batch No. 1: 5 hairs incubated in Williams' medium E (marketed by the company Gibco BRL), to which are added glutamine (2 mM) and antibiotics (penicillin G, 100 units/ml; streptomycin S, 100 μg/ml; amphotericin, 250 ng/ml).

Batch No. 2: 5 hairs incubated in the same medium as above but additionally containing minoxidil at the final concentration of 10 μM.

After 18 hours, the plucked hairs from each group (5 hairs) are collected in a microtube under an argon atmosphere and then stored at −80° C. On the day of the quantitative determination, 250 μl of degassed methanol are added to each tube and then each sample is ground mechanically (10 rotations) using a pestle (tissue grind pestle SZ 20, marketed by the company Kontes). The ground material is then subjected to ultrasound (20 pulses of 1 second; 50% amplitude) using a "Vibra cell 72 434" ultrasonic device (marketed by the company Bioblock Scientific). The ground material which has been subjected to ultrasound is centrifuged at 4° C. at 14000 revolutions/minute for 10 minutes (Eppendorff centrifuge, model 5415C). The supernatant is then collected in a clean tube and lyophilized for one hour. The lyophilisate is taken up in 60 μl of phosphate buffer pH 7.5 supplied in the Biotrak kit (marketed by the company Amersham). The $PGE_2$ contents of 50 μl of this preparation are then evaluated using the Biotrak kit according to the manufacturer's instructions.

|  | Batch No. 1 | Batch No. 2 | % |
|---|---|---|---|
|  | $PGE_2$ in pg/ml | | Inhibition |
| Donor #1 (alopecic) | 15.2 | 5.6 | 63 |
| Donor #2 (alopecic) | 13.7 | 8.5 | 38 |
| Donor #3 (alopecic) | 15.7 | 15.3 | 2.5 |
| Donor #4 (non-alopecic) | 6.2 | 6.2 | 0 |
| Donor #5 (non-alopecic) | 10.7 | 11.2 | 0 |

These examples show that, in vitro, it is possible, by means of a pharmacological agent which is supposed to promote hair regrowth in vivo (i.e. Minoxidil), to decrease the amount of $PGE_2$ produced by the plucked hairs from certain alopecic individuals in the inflammatory stage (donors 1 and 2 in this example).

This observation can indicate a treatment with minoxidil in vivo in these individuals who respond to minoxidil in vitro and, generally, this methodology can indicate the choice of an active ingredient which is active, with respect to the criterion studied (in this case, the production of $PGE_2$), for a specific donor. Conversely, this method of evaluation makes it possible to avoid a restrictive, cumbersome and expensive treatment for a specific subject (example of Donor 3) or when the test shows a response to this active ingredient in the form of a hyperproduction of inflammatory mediators (phenomena of allergy and/or of irritation).

What is claimed is:

1. An assay for determining whether a substance is potentially suitable for usage as an active ingredient in a hair treatment composition which process comprises the following steps:

(i) obtaining at least one plucked hair follicle from a subject;

(ii) placing said at least one plucked hair follicle directly in a culture medium containing nutrients, which culture medium contains a first substance which is to be screened for its suitability as an active ingredient in a hair treating composition or to which culture medium said first substance is added after the addition of said at least one hair follicle;

(iii) incubating said at least one plucked hair follicle with said culture medium containing said first substance which is being screened for its potential suitability as an active ingredient in a hair treating composition for a sufficient amount of time for the production of a second substance which mediates inflammation, the production of which correlates to the potential suitability of said first substance as an active ingredient in a hair treating composition;

(iv) quantitatively assaying for the presence of said second substance which mediates inflammation, and comparing these results to a control hair follicle containing composition which does not contain the first substance; and (v) determining based on the results of said assay the potential suitability of said first substance as an active ingredient in a hair treating composition.

2. The assay of claim 1, wherein the culture medium maintains the viability of said at least one hair follicle for a sufficient time to conduct the assay.

3. The assay of claim 1, wherein the culture medium contains at least one substance which provides for the growth of said at least one hair follicle.

4. The assay of claim 1, wherein the incubating step (iii) is effected for a time period ranging from about 5 seconds to 96 hours.

5. The assay of claim 4, wherein said time period ranges from about 12 to about 24 hours.

6. The assay of claim 1, wherein assay step (iv) measures the concentration, amount or distribution of said second substance in the culture medium or in the hair follicle.

7. The assay of claim 1, wherein the assay step (iv) assays the presence of said second substance which is contained in the hair follicle.

8. The assay of claim 7, wherein the incubated hair follicle is ground prior to conducting the assay step (iv).

9. The assay of claim 1, wherein the screened first substance is selected from the group consisting of nucleic acids, proteins, combinations of different proteins which may be separate or bound to one another, ions, cell organelles, lipids and polysaccharides.

10. The assay of claim 1 wherein the first substance which is being screened for usage as an active ingredient in hair treating compositions putatively affects at least one of the following hair follicle properties; (i) coloration, (ii) survival, (iii) hair loss, (iv) retardation of growth and (iv) enhancing of growth.

11. The assay of claim 1, which is used to identify a substance potentially suitable for treatment of alopecia.

12. The assay of claim 11, wherein alopecia is selected from the group consisting of androgenic alopecia, alopecia areata and alopecia totalis.

13. The assay of claim 1, wherein said assayed second substance is selected from the group consisting of cytokines, chemokines, chemotactic factors responsible for the recruitment of lymphocytes, monocytes, Langerhans cells, and basophils to sites of inflammation, and other factors involved in the inflammatory cascade.

14. The assay of claim 1, wherein said assayed second substance is selected from the group consisting of interleukin-1α, interleukin-1β, interleukin-6, tumor necrosis factors α and β, interleukin-8, monocyte chemotactic and activating factor (MCAF), leukotrienes $B_4$, arachidonic acid and prostaglandins.

15. The assay of claims 14, wherein the assayed prostaglandin is prostaglandin $E_2$.

16. The assay of claim 11, wherein said assayed second substance is selected from the group consisting of cytokines, chemokines, chemotactic factors responsible for the recruitment of lymphocytes, monocytes, Langerhans cells, and basophils to sites of inflammation, and other factors involved in the inflammatory cascade.

17. The assay of claim 11, wherein said assayed second substance is selected from the group consisting of interleukin-1α, interleukin-1β, interleukin-6, tumor necrosis factors α and β, interleukin-8, monocyte chemotactic and activating factor, leukotrienes $B_4$, arachidonic acid and prostaglandins.

18. The assay of claim 1, wherein said assayed second substance is an interleukin.

19. The assay of claim 11, wherein said assayed second substance is an interleukin.

20. The assay of claim 12, wherein the interleukin is selected from the group consisting of interleukin-1α, interleukin-1β, interleukin-6 and interleukin-8.

21. The assay of claim 19, wherein the interleukin is selected from the group consisting of interleukin-1α, interleukin-1β, interleukin-6 and interleukin-8.

22. The assay of claim 20, wherein the assayed interleukin is interleukin-1α.

23. The assay of claim 20, wherein the assayed interleukin is interleukin-8.

24. The assay of claim 21, wherein the assayed interleukin is interleukin-1α.

25. The assay of claim 21, wherein the assayed interleukin is interleukin-8.

26. The assay of claim 1, wherein the assayed second substance is a prostaglandin.

27. The assay of claim 26, wherein the assayed prostaglandin is a prostaglandin $E_2$.

28. The assay of claim 1, wherein the first substance screened for its suitability as an active agent in hair treating compositions is a substance potentially suitable for treating and/or preventing an inflammatory stage of alopecia.

* * * * *